United States Patent [19]

Johnson

[11] 4,181,808

[45] Jan. 1, 1980

[54] 5-KETO PROSTAGLANDIN Fα ANALOGS

[75] Inventor: Roy A. Johnson, Kalamazoo, Mich.

[73] Assignee: The Upjohn Company, Kalamazoo, Mich.

[21] Appl. No.: 932,898

[22] Filed: Aug. 11, 1978

Related U.S. Application Data

[60] Division of Ser. No. 819,856, Jul. 28, 1977, Pat. No. 4,123,441, which is a continuation-in-part of Ser. No. 725,546, Sep. 22, 1976, abandoned, which is a continuation-in-part of Ser. No. 716,960, Aug. 23, 1976, abandoned.

[51] Int. Cl.$^2$ ............................................. C07C 177/00
[52] U.S. Cl. ...................................... 560/121; 562/503
[58] Field of Search ........................ 560/121; 562/503

[56] References Cited

U.S. PATENT DOCUMENTS 4,131,738  12/1978  Smith .................................... 560/121

Primary Examiner—Robert Gerstl
Attorney, Agent, or Firm—Morris L. Nielsen

[57] ABSTRACT

Prostaglandin (PG$_1$) derivatives having (1) a 5-keto feature, for example

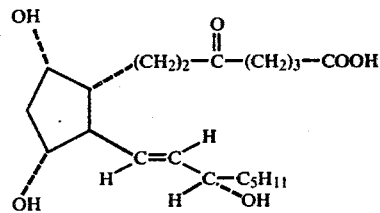

or (2) a 9-deoxy-5,9-epoxy feature together with a 4-halo or 5-hydroxy feature, for example

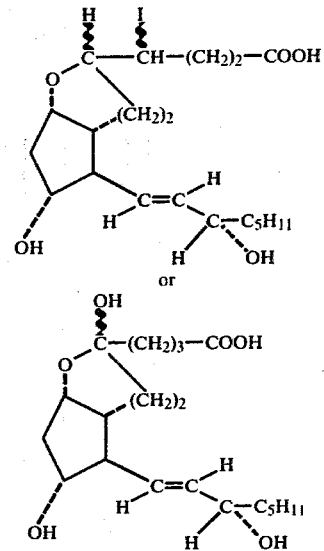

or a 4,5-didehydro feature, for example in an enol ether of the formula

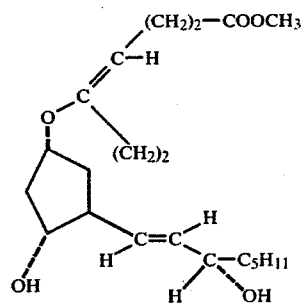

said derivatives having pharmacological activity. Processes for preparing them and the appropriate intermediates are disclosed.

20 Claims, No Drawings

5-KETO PROSTAGLANDIN Fα ANALOGS

CROSS REFERENCE TO THE RELATED APPLICATIONS

This application is a division of Ser. No. 819,856, filed July 28, 1977, now issued as U.S. Pat. No. 4,123,441, which was a continuation-in-part of then copending application Ser. No. 725,546, filed Sept. 22, 1976, since abandoned, which was a continuation-in-part of then copending application Ser. No. 716,960, filed Aug. 23, 1976, since abandoned.

The essential material for this application, including the background of the invention, the disclosure of the invention, and the description of the preferred embodiments, including Preparations and Examples, is incorporated by reference from issued U.S. Pat. No. 4,123,441, under the provisions of M.P.E.P. 608.01(p).

BACKGROUND OF THE INVENTION

This invention relates to prostaglandin derivatives and to a process for preparing them.

The prostaglandins and analogs are well-known organic compounds derived from prostanoic acid which has the following structure and atom numbering:

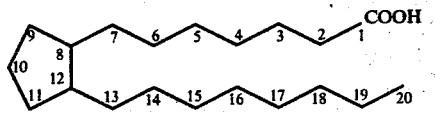

As drawn hereinafter the formulas represent a particular optically active isomer having the same absolute configuration as PGE$_1$ obtained from mammalian tissues.

In the formulas, broken line attachments to the cyclopentane ring or side chain indicate substituents in alpha configuration, i.e. below the plane of the ring or side chain. Heavy solid line attachments indicate substituents in beta configuration, i.e. above the plane.

For background on prostaglandins, see for example Bergstrom, et al., Pharmacol. Rev. 20, 1 (1968). For related compounds see Pace-Asciak, et al., Biochem. 10, 3657 (1971). Related compounds are described in a publication on 6-keto-prostaglandin F$_{1\alpha}$ by Pace-Asciak, J. Am. Chem. Soc. 98, 2348 (1976) and a publication on "PGX" (6,9α-oxido-9α,15α-dihydroxyprosta-(Z)5,(E)13-dienoic acid) by E. J. Corey, et al., J. Am. Chem. Soc. 99, 20006 (1977).

Some of the compounds of this invention may be regarded as analogs of prostacyclin and prostacyclin-type compounds.

Prostacyclin, an organic compound related to prostaglandins, is (5Z)-9-deoxy-6,9α-epoxy-Δ$^5$-PGF$_1$ and is represented by the formula

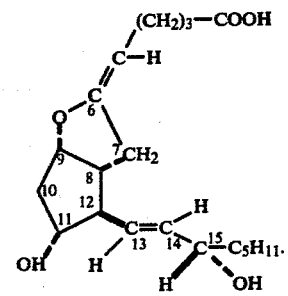

For its synthesis and structure see for example R. A. Johnson et al., J. Am. Chem. Soc. 99, 4182 (1977) and Prostaglandins 12, 915 (1976), and E. J. Corey, et al., cited above. For some of its biological properties and uses see the references cited in the Johnson references. Prostacyclin is referred to as "PGI$_2$", see Anonymous, Prostaglandins 13, 375 (1977).

SUMMARY OF THE INVENTION

It is the purpose of this invention to provide novel products having pharmacological activity. It is a further purpose to provide processes for preparing these products and their intermediates.

Accordingly, there is provided a compound of the formula:

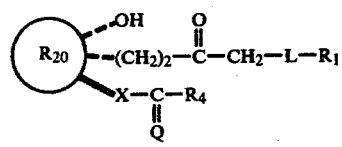

or a mixture comprising that compound and the enantiomer thereof wherein $R_{20}$ is

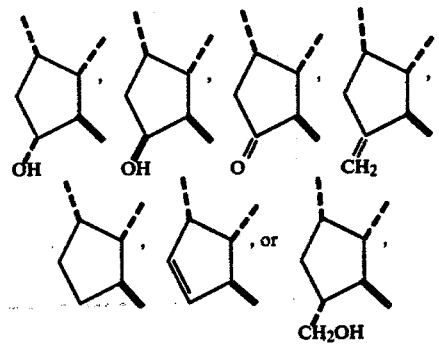

wherein L is
(1) —(CH$_2$)$_d$-C(R$_2$)$_2$—
(2) —O—CH$_2$—Y— or
(3) —CH=CH—
 wherein d is zero to 5, R$_2$ is hydrogen, methyl, or fluoro, being the same or different with the proviso that one R$_2$ is not methyl when the other is fluoro, and Y is a valence bond, —CH$_2$— or —(CH$_2$)$_2$—,
wherein Q is

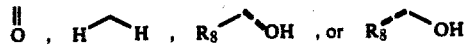

wherein R$_8$ is hydrogen or alkyl of one to 4 carbon atoms, inclusive,
wherein R$_1$ is (1) —COOR$_3$
(2) —CH$_2$OH
(3) —CH$_2$N(R$_9$)(R$_{18}$)
(4) 
$$-\overset{O}{\underset{\|}{C}}-N(R_9)(R_{18})$$ or
(5) 
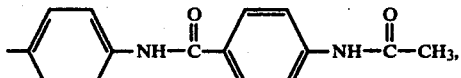

wherein R$_3$ is (a) hydrogen, (b) alkyl of one to 12 carbon atoms, inclusive, (c) cycloalkyl of 3 to 10 carbon atoms, inclusive, (d) aralkyl of 7 to 12 carbon atoms, inclusive, (e) phenyl, (f) phenyl substituted with one, 2, or 3 chloro or alkyl of one to 4 carbon atoms, inclusive, (g) 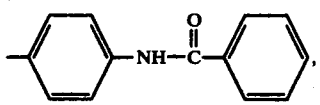

(h) 

(i)

(j)

(k)

(l)

(m) 
$$-\overset{O}{\underset{\underset{R_{11}}{|}}{\overset{|}{C}H}}-\overset{\|}{C}-R_{10},$$

wherein R$_{10}$ is phenyl, p-bromophenyl, p-biphenylyl, p-nitrophenyl, p-benzamidophenyl, or 2-naphthyl, and wherein R$_{11}$ is hydrogen or benzoyl, or (n) a pharmacologically acceptable cation, wherein R$_8$ is hydrogen, methyl, or ethyl, and R$_{18}$ is hydrogen, alkyl of one to 4 carbon atoms, inclusive, aralkyl of 7 to 12 carbon atoms, inclusive, phenyl, or phenyl substituted with alkyl of one to 4 carbon atoms, inclusive;
wherein R$_4$ is (1) 
$$-\overset{R_5}{\underset{R_6}{\overset{|}{\underset{|}{C}}}}-C_gH_{2g}-CH_3$$

(2) 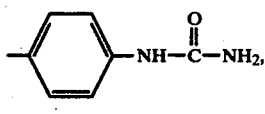

(3) 
$$-CH_2\underset{H}{\overset{}{\underset{}{C}}}=\overset{}{\underset{H}{C}}\overset{CH_2CH_3}{}$$

wherein C$_g$H$_{2g}$ is alkylene of one to 9 carbon atoms, inclusive, with one to 5 carbon atoms, inclusive, in the chain between —CR$_5$R$_6$— and terminal methyl, wherein R$_5$ and R$_6$ are hydrogen, alkyl of one to 4 carbon atoms, inclusive, or fluoro, being the same or different, with the proviso that one of R$_5$ and R$_6$ is fluoro only when the other is hydrogen or fluoro and the further proviso that neither R$_5$ nor R$_6$ is fluoro when Z is oxa (—O—); wherein Z represents an oxa atom (—O—) or C$_j$H$_{2j}$ wherein C$_j$H$_{2j}$ is a valence bond or alkylene of one to 9 carbon atoms, inclusive, with one to 6 carbon atoms, inclusive between CR$_5$R$_6$— and the phenyl ring; wherein T is alkyl of one to 4 carbon atoms, inclusive, fluoro, chloro, trifluoromethyl, or —OR$_7$— wherein R$_7$ is alkyl of one to 4 carbon atoms, inclusive, and s is zero, one, 2 or 3, with the proviso that not more than two T's are other than alkyl and when s is 2 or 3 the T's are either the same or different; and
wherein X is (1) trans-CH=CH—
(2) cis-CH=CH—
(3) —C≡C— or
(4) —CH$_2$CH$_2$—;
including the lower alkanoates thereof.

In formula I as used herein, attachment to 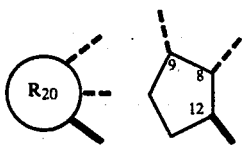 corresponds to bonds to the cyclopentane ring at the C-8, C-9, and C-12 positions following prostaglandin nomenclature, thus:

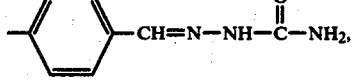

Within the scope of the prostaglandin derivatives described herein there are represented (a) PGF$_\alpha$ compounds when 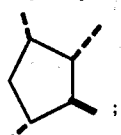 is

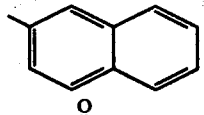

(b) 11β-PGF$_\alpha$ compounds when 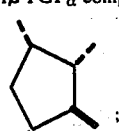 is (c) 11-Deoxy-11-keto-PGF$_\alpha$ compounds when (R$_{20}$) is -continued

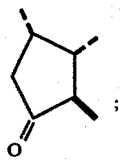
(d) 11-Deoxy-11-methylene-PGF$_\alpha$ compounds when ⓇR$_{20}$ is

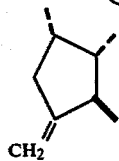
(e) 11-Deoxy-PGF$_\alpha$ compounds when ⓇR$_{20}$ is

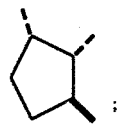
(f) 11-Deoxy-10,11-Didehydro-PGF$_\alpha$ compounds when ⓇR$_{20}$ is

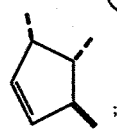
; and (g) 11-Deoxy-11-hydroxymethyl-PGF$_\alpha$ compounds when ⓇR$_{20}$ is

For those compounds of formula I wherein Q is

i.e. wherein the C-15 hydroxyl group is attached to the side chain in alpha configuration, the configuration at C-15 is identical with that of the naturally occuring prostaglandins such as PGE$_1$ obtained from mammalian tissues. The 15-epimer compounds are represented by formula I when Q is

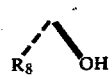

and are identified variously as "15-epi" or "15β" or "15R" by the appropriate prefix in the name. As is known in the art. "R" and "S" designations depend on the neighboring substituents. See R. S. Cahn, J. Chem. Ed. 41, 116 (1964).

A typical example of the keto compounds of formula I is represented by the formula

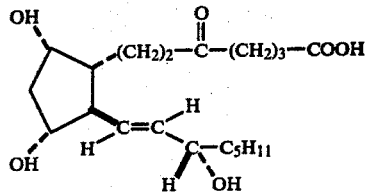

named 5-keto-PGF$_{1\alpha}$. The compound of formula V is a species of the formula-I compounds wherein ⓇR$_{20}$ is

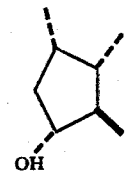

L is —(CH$_2$)$_2$—, Q is

R$_1$ is —COOH, R$_4$ is n-pentyl, and X is trans-CH=CH—.

I claim:
1. A compound of the formula

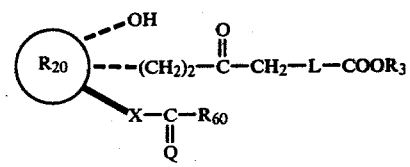

wherein ⓇR$_{20}$ is

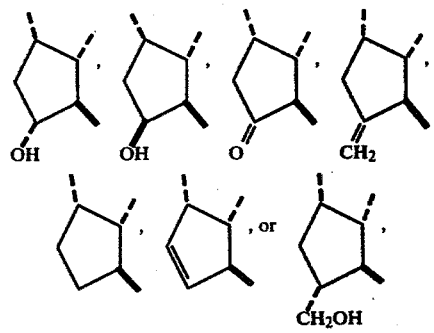

wherein L is
(1) —(CH$_2$)$_d$-C(R$_2$)$_2$—
(2) —O—CH$_2$—Y— or
(3) —CH=CH—
wherein d is zero to 5, R$_2$ is hydrogen, methyl, or fluoro, being the same or different with the proviso that one R$_2$ is not methyl when the other is fluoro, and Y is a valence bond, —CH$_2$—, or —(CH$_2$)$_2$—,
wherein Q is

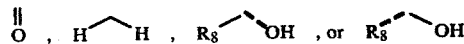

wherein R$_8$ is hydrogen or alkyl of one to 4 carbon atoms, inclusive, wherein R$_3$ is (a) hydrogen, (b) alkyl of one to 12 carbon atoms, inclusive, (c) cycloalkyl of 3 to 10 carbon atoms, inclusive, (d) aralkyl of 7 to 12 carbon atoms, inclusive, (e) phenyl, (f) phenyl substituted with one, 2, or 3 chloro or alkyl of one to 4 carbon atoms, inclusive,

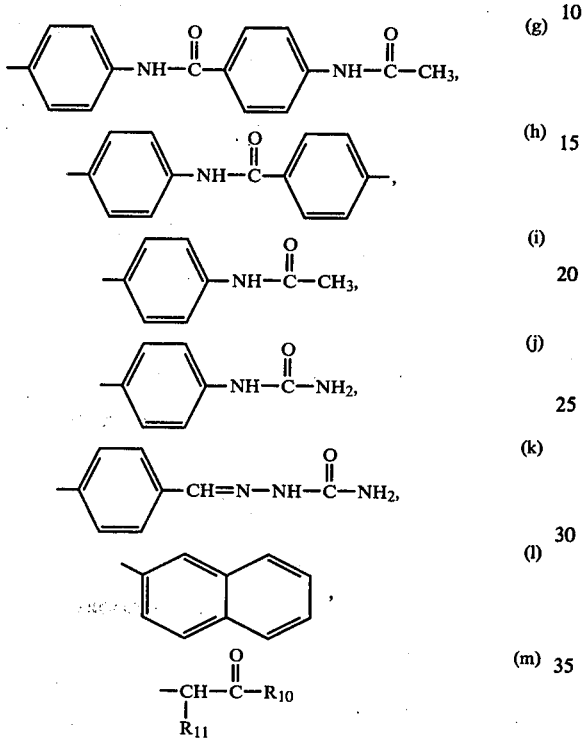

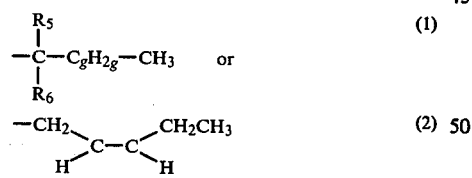

wherein R$_{10}$ is phenyl, p-bromophenyl, p-biphenylyl, p-nitrophenyl, p-benzamidophenyl, or 2-naphthyl, and wherein R$_{11}$ is hydrogen or benzoyl, or (n) a pharmacologically acceptable cation,
wherein R$_{60}$ is $$-\overset{R_5}{\underset{R_6}{\overset{|}{\underset{|}{C}}}}-C_gH_{2g}-CH_3 \quad \text{or} \quad (1)$$

$$-CH_2\diagdown\underset{H}{C}-\underset{H}{C}\diagup CH_2CH_3 \quad (2)$$

wherein C$_g$H$_{2g}$ is alkylene of one to 9 carbon atoms, inclusive, with one to 5 carbon atoms, inclusive, in the chain between —CR$_5$R$_6$— and terminal methyl, wherein R$_5$ and R$_6$ are hydrogen, alkyl of one to 4 carbon atoms, inclusive, or fluoro, being the same or different, with the proviso that one of R$_5$ and R$_6$ is fluoro only when the other is hydrogen or fluoro,
wherein X is
  (1) trans-CH═CH—
  (2) cis-CH═CH—
  (3) —C≡C— or
  (4) —CH$_2$CH$_2$—, and
wherein wavy line (∼) indicates attachment in alpha or beta configuration.

2. A compound according to claim 1 wherein (R$_{20}$) is

3. A compound according to claim 1 wherein (R$_{20}$) is

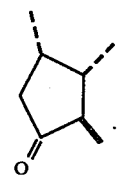

4. A compound according to claim 1 wherein (R$_{20}$) is

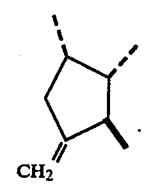

5. A compound according to claim 1 wherein (R$_{20}$) is

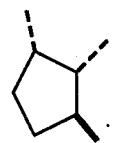

6. 5-Keto-11-deoxy-PGF$_{1\alpha}$, methyl ester, a compound according to claim 5.

7. A compound according to claim 1 wherein (R$_{20}$) is

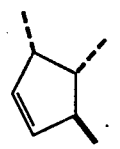

8. A compound according to claim 1 wherein (R$_{20}$) is

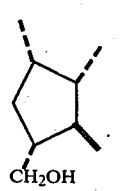

9. A compound according to claim 1 wherein (R$_{20}$) is

10. A compound according to claim 9 wherein L is —(CH$_2$)n, n being 2, 3, or 4, wherein Q is

wherein R$_8$ is limited to hydrogen, methyl, or ethyl, and wherein R$_4$ is n-pentyl, 1,1-dimethylpentyl, or 1,1-difluoropentyl.

11. A compound according to claim 10 wherein X is —C≡C—.

12. A compound according to claim 10 wherein X is —CH$_2$CH$_2$—.

13. 5-Keto-13,14-dihydro-PGF$_{1\alpha}$, a compound according to claim 12.

14. 5-Keto-13,14-dihydro-PGF$_{1\alpha}$, methyl ester, a compound according to claim 12.

15. 5,15-Diketo-13,14-dihydro-PGF$_{1\alpha}$, a compound according to claim 12.

16. A compound according to claim 10 wherein X is trans—CH=CH—.

17. A compound according to claim 16 wherein R$_3$ is hydrogen, alkyl of one to 12 carbon atoms, inclusive, or a pharmacologically acceptable cation.

18. 5-Keto-PGF$_{1\alpha}$, a compound according to claim 17.

19. 5-Keto-PGF$_{1\alpha}$, methyl ester, a compound according to claim 17.

20. 5,15-Diketo-PGF$_{1\alpha}$, a compound according to claim 17.

* * * * *

UNITED STATES PATENT OFFICE
CERTIFICATE OF CORRECTION

Patent No. 4,181,808         Dated 1 January 1980

Inventor(s) Roy A. Johnson

It is certified that error appears in the above-identified patent and that said Letters Patent are hereby corrected as shown below:

In the Abstract, line 1, "(PG$_1$ derivatives" should read -- (PG$_1$) derivatives --; that portion of the last formula reading

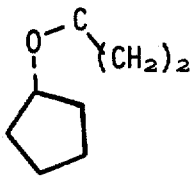      should read      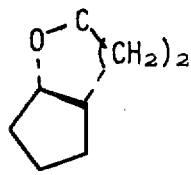

Column 1, lines 32-38,

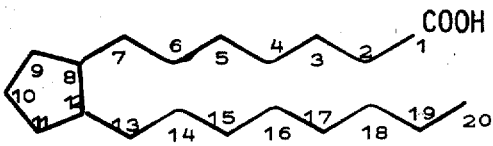

should read

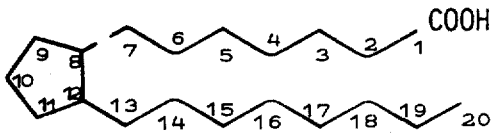

UNITED STATES PATENT OFFICE
CERTIFICATE OF CORRECTION

Patent No. 4,181,808  Dated 1 January 1980

Inventor(s) Roy A. Johnson

It is certified that error appears in the above-identified patent and that said Letters Patent are hereby corrected as shown below:

Column 7, lines 50-53,

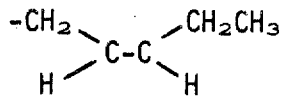  should read  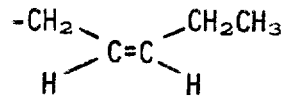

Signed and Sealed this

*Seventh* Day of *April 1981*

[SEAL]

Attest:

Attesting Officer

RENE D. TEGTMEYER

*Acting Commissioner of Patents and Trademarks*